(12) United States Patent
Riesinger

(10) Patent No.: US 7,959,624 B2
(45) Date of Patent: Jun. 14, 2011

(54) DEVICE FOR THE TREATMENT OF WOUNDS USING A VACUUM

(75) Inventor: Birgit Riesinger, Ostbevern (DE)

(73) Assignee: Birgit Riesinger, Münster (DE)

( * ) Notice: Subject to any disclaimer, the term of this patent is extended or adjusted under 35 U.S.C. 154(b) by 0 days.

(21) Appl. No.: 11/666,958

(22) PCT Filed: Nov. 2, 2005

(86) PCT No.: PCT/EP2005/011692
§ 371 (c)(1),
(2), (4) Date: Jul. 5, 2007

(87) PCT Pub. No.: WO2006/048240
PCT Pub. Date: May 11, 2006

(65) Prior Publication Data
US 2008/0009812 A1    Jan. 10, 2008

(30) Foreign Application Priority Data
Nov. 2, 2004   (DE) ............... 20 2004 017 052 U

(51) Int. Cl.
*A61M 27/00*   (2006.01)
*A61M 1/00*   (2006.01)
*A61M 35/00*   (2006.01)
*A61F 13/00*   (2006.01)

(52) U.S. Cl. ........ 604/543; 604/540; 604/541; 604/313; 604/315; 604/316; 604/304; 604/305; 604/308; 604/289; 604/290

(58) Field of Classification Search .................. 604/305, 604/306, 307, 308
See application file for complete search history.

(56) References Cited

U.S. PATENT DOCUMENTS
3,111,948 A * 11/1963 Burgeni ................ 604/365
(Continued)

FOREIGN PATENT DOCUMENTS
DE    29 53 373 C2    6/1979
(Continued)

OTHER PUBLICATIONS
International Search Report (WO2008/040681 dated Feb. 19, 2008).
(Continued)

*Primary Examiner* — Tatyana Zalukaeva
*Assistant Examiner* — Susan Su
(74) *Attorney, Agent, or Firm* — Occhiuti Rohlicek & Tsao LLP

(57) ABSTRACT

The invention relates to a device (100) for treating wounds of the human or animal body using a vacuum and having a gas-tight wound-covering element (4), which, when placed in contact with the body of the patient, forms a wound space (10) between the respective wound and the wound-covering element, at least one connecting site (5.1; 5.2), which is in contact with the wound space (10), an absorption body (2), which is a layer, enclosed in an envelope, of a textile section, interspersed with super-absorbing particles, the envelope being permeable to liquids and having pores, the size of which does not exceed that of the super-absorbing particles. The absorption body (2), which is to be inserted in the wound space (10), has an initial volume, which enlarges in the course of the absorption process, and a final volume, so that, due to the size of the pores of the envelope, the absorbed wound secretions remain within the absorption body (2) and, with that, below the wound-covering element, until the absorption body is removed from the wound space.

26 Claims, 9 Drawing Sheets

U.S. PATENT DOCUMENTS

| | | | |
|---|---|---|---|
| 3,364,931 A * | 1/1968 | Hirsch | 604/366 |
| 3,871,376 A | 3/1975 | Kozak | |
| 3,872,862 A | 3/1975 | Hume | |
| 4,382,441 A | 5/1983 | Svedman | |
| 4,592,750 A | 6/1986 | Kay | |
| 4,969,880 A | 11/1990 | Zamierowski | |
| 5,086,763 A | 2/1992 | Hathman | |
| 5,383,871 A * | 1/1995 | Carlin et al. | 604/385.29 |
| 5,476,664 A | 12/1995 | Robinson et al. | |
| 5,487,889 A * | 1/1996 | Eckert et al. | 424/93.1 |
| 5,540,922 A * | 7/1996 | Fabo | 424/402 |
| 5,549,584 A | 8/1996 | Gross | |
| 5,636,643 A * | 6/1997 | Argenta et al. | 128/897 |
| 6,071,267 A * | 6/2000 | Zamierowski | 604/289 |
| 6,171,306 B1 | 1/2001 | Fleischman et al. | |
| 6,191,341 B1 * | 2/2001 | Shippert | 604/383 |
| 6,333,093 B1 * | 12/2001 | Burrell et al. | 428/194 |
| 6,398,767 B1 * | 6/2002 | Fleischmann | 604/313 |
| 6,626,891 B2 * | 9/2003 | Ohmstede | 604/543 |
| 6,685,681 B2 | 2/2004 | Lockwood et al. | |
| 6,966,901 B2 | 11/2005 | Leisner | |
| 7,048,706 B2 | 5/2006 | Cea | |
| 7,524,315 B2 * | 4/2009 | Blott et al. | 604/543 |
| 2002/0065494 A1 | 5/2002 | Lockwood et al. | |
| 2004/0030304 A1 | 2/2004 | Hunt et al. | |
| 2004/0054338 A1 | 3/2004 | Bybordi | |
| 2006/0009744 A1 | 1/2006 | Erdman | |
| 2008/0004559 A1 | 1/2008 | Riesinger | |
| 2008/0119802 A1 | 5/2008 | Riesinger | |

FOREIGN PATENT DOCUMENTS

| | | |
|---|---|---|
| DE | 2953373 | 6/1979 |
| DE | E33 446 B | 10/1984 |
| DE | 35 50 798 | 10/1988 |
| DE | 195 17 699 A1 | 5/1995 |
| DE | 19517699 | 5/1995 |
| DE | 100 59 439 | 12/2005 |
| EP | 0762860 | 3/1997 |
| EP | 1 129 734 | 9/2001 |
| EP | 1 177 781 A | 2/2002 |
| GB | 692578 | 9/1950 |
| GB | 2272645 | 5/1994 |
| WO | WO83/02054 | 6/1983 |
| WO | 96/05873 | 2/1996 |
| WO | 99/01173 | 1/1999 |
| WO | 01/10363 | 2/2001 |
| WO | 01/89431 | 11/2001 |
| WO | 03/094813 | 11/2003 |
| WO | 2005/123170 | 12/2005 |
| WO | WO2006/048246 | 5/2006 |
| WO | WO2006/056294 | 6/2006 |
| WO | WO2008/040681 | 4/2008 |

OTHER PUBLICATIONS

International Preliminary Report on Patentability (WO2008/040681 dated Apr. 7, 2009).
International Search Report (WO2006/048240 mailed Mar. 9, 2006).
International Preliminary Report on Patentability (WO2006/048240 dated May 8, 2007).
International Search Report (WO2006/048246 dated Jun. 3, 2006).
International Preliminary Report on Patentability (WO2006/048246 dated May 22, 2007).
International Search Report (WO2006/056294 dated Apr. 10, 2006).
International Preliminary Report on Patentability (WO2006/056294 dated May 30, 2007).

* cited by examiner

DEVICE FOR THE TREATMENT OF WOUNDS USING A VACUUM

BACKGROUND OF THE INVENTION

The invention relates to a device for the treatment of wounds of the human or animal body using a vacuum, comprising a gas-tight wound-covering element which, when placed in contact with the body of the patient, forms a wound space remaining between the respective wound and the wound-covering element, at least one connecting site, which is in contact with the wound space and over which the air in the wound space can be evacuated, and at least one two-dimensional absorption body, which is to be disposed in the wound space below the wound covering element.

US 2004/0030304 A1 discloses a device for the vacuum treatment of wounds, which has an enveloped, foam-like absorption body, the envelope of which has perforations approximately 3 to 6 mm in size. There are also perforations at the absorption body. Furthermore, an additional liquid-permeable foam material is disposed above the enveloped absorption body. The effect of the device is based on the known principle of wound drainage, for which the wound exudate is withdrawn by means producing a vacuum. The withdrawal by atmospheric means is supported by pores of the appropriate size.

The DE 195 17 699 discloses a device for vacuum-sealing a wound, which comprises a covering film for the two-dimensional covering and the air-tight closing of the wound, so that a space, in which the drainage tube and a foam material insert can be inserted, is formed below the covering film in the region of the wound.

The older DE 29 53 373 C2 patent also discloses a device for the treatment of wounds using a vacuum, comprising a wound covering element, a foam material insert below the wound covering element and at least one hose connection, which communicates with the pores of the foam material insert.

A further device for the treatment of wounds using vacuum is disclosed in U.S. Pat. No. 6,685,681 B2, for which an elastic pressure-distributing element, to which a suction tube is connected in turn, is placed on the surface of the wound. The suction tube passes between the edge of the wound and a wound-covering element, which is glued thereon. The wound space, bounded by the wound-covering element and the pressure-distributing element, is filled with cellulose, the size of which essentially does not exceed that of the super-absorbing particles.

The GB 6 92 578 shows a drape, the edge of the central opening of which has a peripheral, polymeric adhesive layer, with which the drape can be fastened to the skin of the patient, at its edge.

U.S. Pat. No. 5,549,584 shows a device for vacuum treatment, which consists of a wound covering, a membrane pump and a pouch-like collector, downstream from the membrane pump. A pad or a loose bed of liquid-absorbing fibers, resting on a perforated layer, underneath which there is a further adhesive layer, is disposed underneath the wound covering. The fibers are covered by a liquid-permeable, upper layer, having several windows, there being a material section, which is also permeable to liquids, below each window. The suction head, so designed, appears to be complicated and expensive to produce.

SUMMARY OF THE INVENTION

It is an object of the invention to design a cost effective device for the vacuum treatment of wounds, the design of which is simplified.

This objective is accomplished by a device of the type described above, wherein the absorption body has a textile section, which is enclosed in an envelope and interspersed with super-absorbing particles, the envelope being permeable to liquids and having pores, essentially of the same size as that of the super-absorbing particles.

The absorption body, which is to be placed in the wound space, has an initial volume, which increases in the course of the absorption process and assumes a final volume, so that the wound secretions absorbed, due to the size of the pores in the envelope, remain within the absorption body and, with that, below the wound-covering element until the absorption body is removed from the wound space. The layer, in a plan view of its flat side, has an areal extent, which is 3% to 90% smaller than that of the envelope, when the latter is placed flat.

The textile section of the absorption body consists preferably of cellulose fibers. The device may contain a protective element, which is compatible with mucous membranes and extends on a side of the absorption body opposite to the wound covering element. The area of the protective element is approximately equal to that of the enveloped absorption body and preferably is a little larger. In its simplest embodiment, the mucous membrane-compatible protective element may be film-like. It may also consist of a soft, open cell foam material or of a very loose nonwoven fabric. Finally the protective element may be a loose bed of nonwoven or foam pieces, which are underneath the absorption body and, after the absorption process is finished, may be removed from the wound, for example, with forceps. Moreover, a voluminous formation fulfills not only the function of protecting the mucous membrane, but also that of an absorber. The open cell foam material or the nonwoven fabric may have pores, which are several times larger than those of the envelope, so that the larger particles of wound exudate can be absorbed.

The liquid impermeable wound-covering element preferably consists of a film-like material, which is so stiff, that it does not shrink under normal conditions, that is, in the not used state and in the state, in which it is placed in contact with the body of the patient. Furthermore, it is possible to replace the flat, film-like wound-covering element by a shell-shaped, also film-like and preferably transparent covering, which is provided with a flat border strip for adhesion to the skin. A shell-shaped or bell-shaped covering can be produced cost-effectively by a thermoforming process.

The wound-covering element may be transparent at least at one part of its surface, so that the state of the healing of the wound can be observed. It may be possible to print on the outside of the wound-covering element. The absorption body may be glued to the wound-covering element at least at points, leaving a periphery of the wound covering element free.

The concept of "connecting site" is understood to be essentially an outlet opening, which may be incorporated in the wound-covering element, and to which a hose line and/or a pressure manometer, a vacuum pump, a vacuum bottle and the like may be connected or incorporated into a valve. However, the connecting site may be replaced by a liquid-impermeable and gas impermeable piece of an elastomer, which may be pierced by a needle, such as a syringe needle and, after the needle has been pulled out, retracts to its original shape.

A unidirectional check valve, for example, a valve device known from the air mattresses or water wings or a microvalve, known from medical technology, may be used as a valve.

The vacuum in the space below the wound covering element may be produced manually, mechanically or electrically by means of a device, glued to the body of the patient. A vacuum can be generated manually most easily by means of an injection syringe, a so-called scissors grip vacuum pump or known rubber bellows ("ball pump"), which can be compressed by hand. Different conventional, commercial vacuum pumps, which can be supplied, for example, with a hose and a pressure regulator, are suitable for producing a vacuum electrically. For wound healing processes, which take a longer time, it is necessary to check and maintain the vacuum regularly. This task can be accomplished owing to the fact that the gases, which collect, can be withdrawn from the space, as required, with the simplest of means, in much the same way as blood samples are taken, in that the syringe needle is inserted into the rubber valve or into the hose. The magnitude of the vacuum can be determined with the help of a pressure manometer, which is connected to the outlet opening, or of an installed vacuum indicator. Of course, it is also possible to use vacuum pumps.

In plan view, the device may be polygonal, oval or circular.

The envelope consists of a liquid-permeable, mucous membrane-compatible natural material or plastic, to which the wound secretions adhere hardly, if at all. This enables liquid wound secretions to be transported into the absorption material. The wound secretions pass through the envelope and are absorbed by the absorption material, which has been enriched with super-absorbents.

The envelope, as well as the absorption material within the envelope, may be provided with an odor-inhibiting and/or neutralizing or masking additive, such as an activated charcoal filter. It is of great advantage that, during the evacuation of the gases, wound secretion particles are not carried along. These remain within the envelope of the absorption body until the whole device is removed from the body of the patient and disposed of or until the swollen absorption body is exchanged.

Advantageously, a peripheral overhang of envelope material is left at the envelope of the absorption body, so that any painful contact of the relative hard seam with the surface of the wound can be limited or even avoided. The envelope material between the seam and the outer extent of the envelope is understood to be the overhang here.

A pressure distributor, which is located between the wound-covering element and the enveloped absorption body, may be disposed below the wound covering element. The pressure distributor may be a template of a gas-permeable foam, in which several air paths are present for a uniformly distributed flow of air.

The pressure distributor may also be formed at least partially by a loop-like or meandering end piece of the suction tube passed through the connection site. The end piece of the suction tube may be embedded in a foam piece, which preferably is flat and is to be contacted with the absorption body. Overall, a device is created for treating wounds using a vacuum, for which the wound secretions are aspirated by the nonwoven material of the absorption body, interspersed with super-absorbers and remain within the envelope surrounding the absorption body, without getting back from the envelope into the covered space, the cross-sectional area of the absorption body increasing greatly, by a multiple as the absorption increases and approaching a circular shape and wound secretions hardly being carried along while the vacuum is being maintained by means of an injection syringe or vacuum pump, which can be connected to the device, that is, during the evacuation of gases. Moreover, it is possible to do without an additional collecting container and drainage hose. In use, the device is more comfortable for the patient.

For a full understanding of the present invention, reference should now be made to the following detailed description of the preferred embodiments of the invention as illustrated in the accompanying drawings.

DESCRIPTION OF THE PREFERRED EMBODIMENTS

Figure 1A:
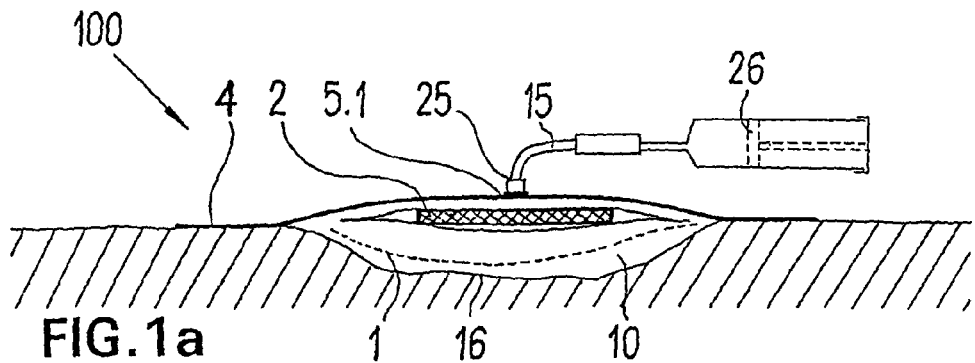
FIGS. 1a to 1d show a preferred embodiment of a device according to the invention, glued to the skin of the patient, in a diagrammatic section.
Figure 1B:
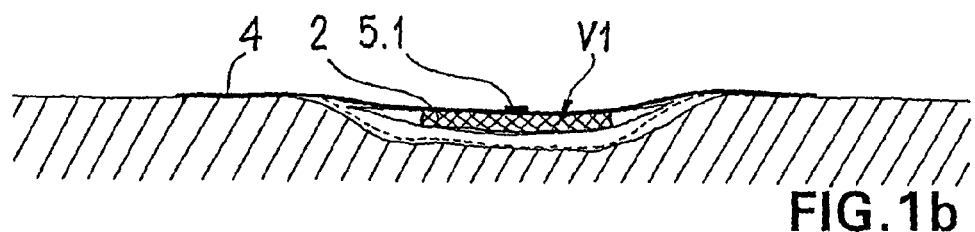
Figure 1C:
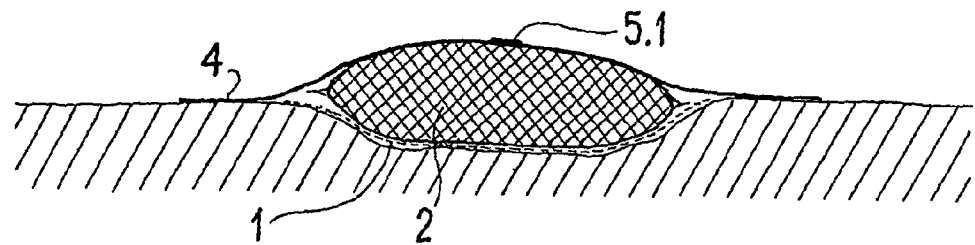
Figure 1D:
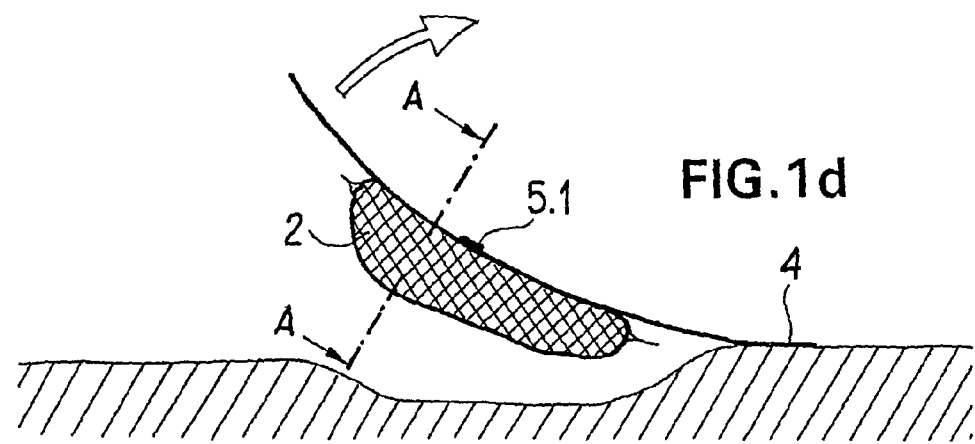
Figure 2:
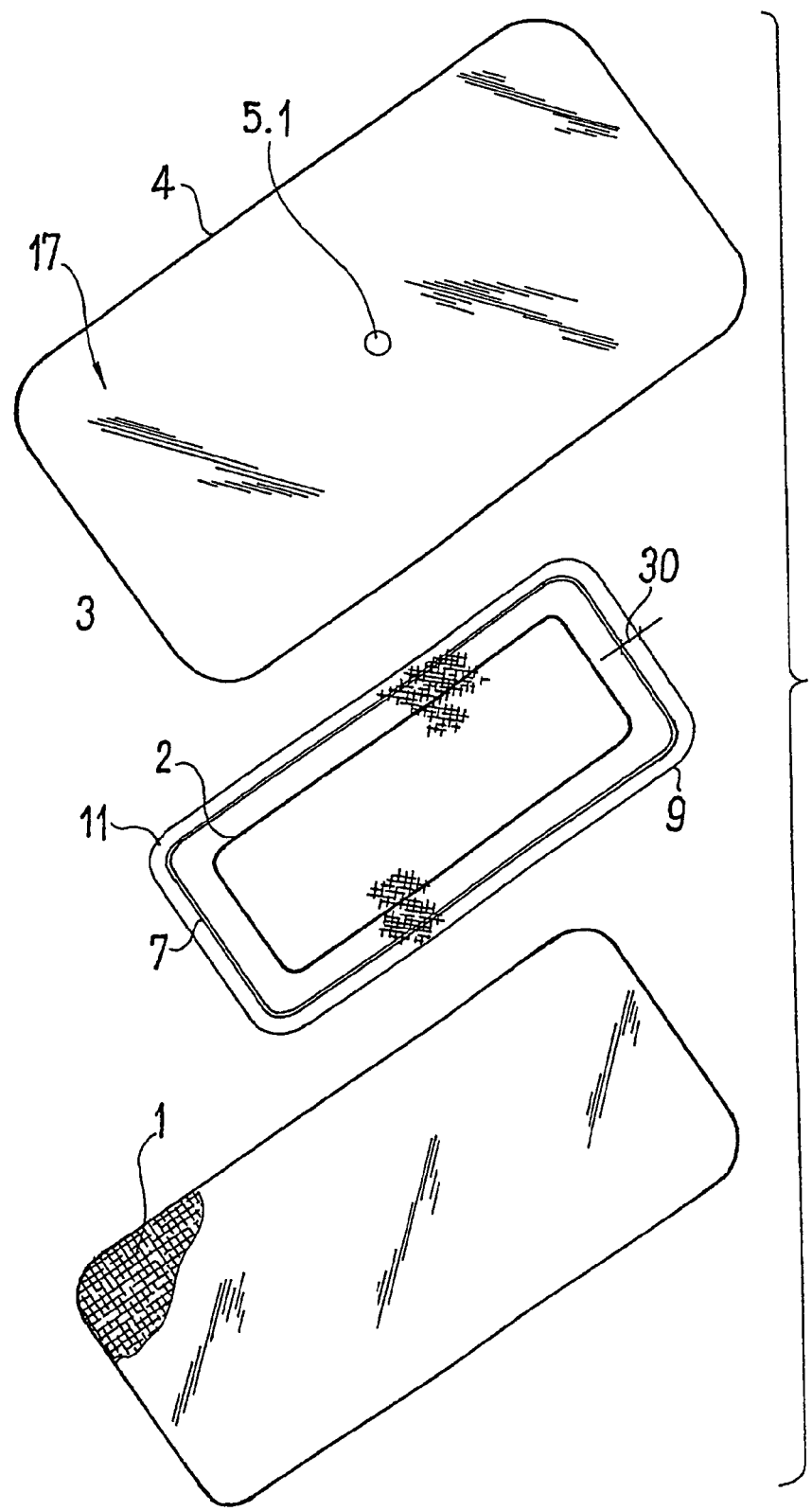
FIG. 2 shows the device of FIG. 1 in an exploded representation.
Figure 3:
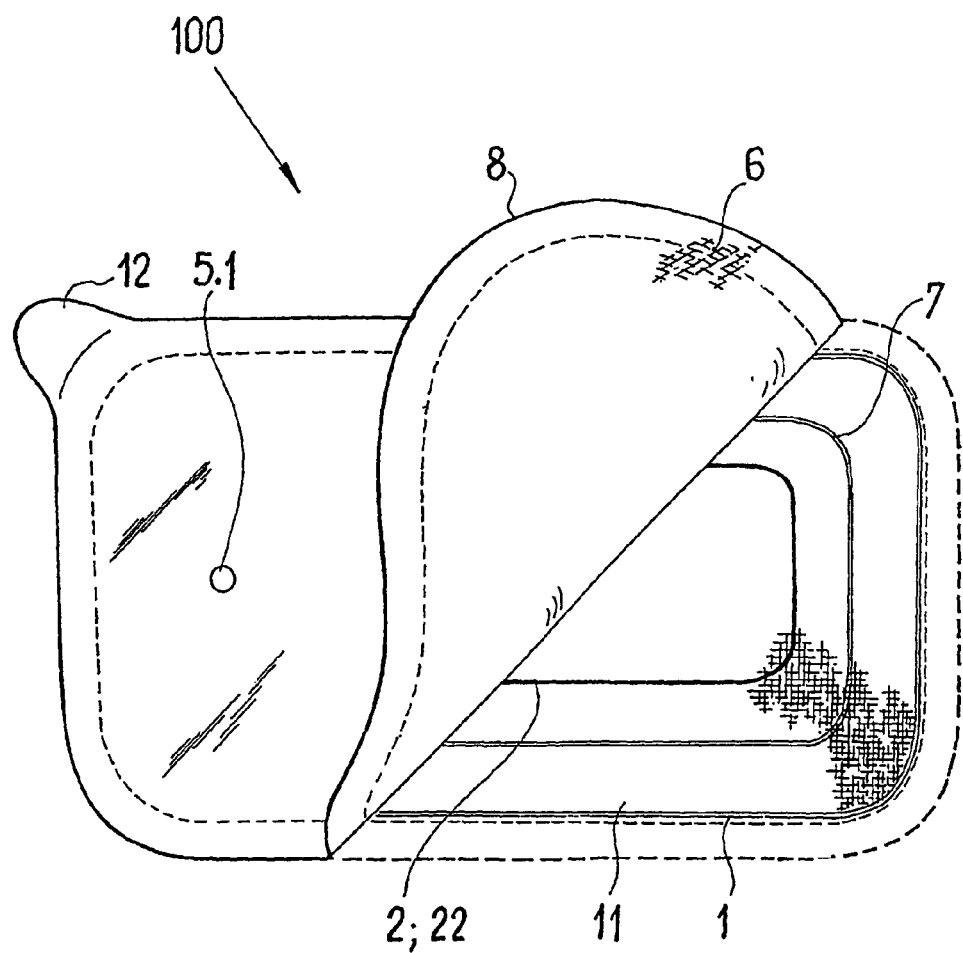
FIG. 3 shows the device of FIG. 1 in a plan view of the wound-covering element.

The preferred embodiments of the present invention will now be described with reference to FIGS. 1-10 of the drawings. Identical elements in the figures are designated with the same reference numerals.

FIGS. 1a to 1d, 2, 3 and 8 show a device 100 for the treatment of wounds, consisting of a film-like wound covering element 4, a mucous membrane-compatible film element 1 and, between these, the absorption body 2. In plan view of its flat side, the device is approximately rectangular and has rounded corners 3. At least at one corner of the wound-covering element 4, a pull-off tab 12 is attached. Moreover, sterile, air-tight packaging (not shown) is provided.

The wound-covering element 4, consisting of a liquid-impermeable, transparent film, is relatively stiff, that is, it does not shrink when it is not in use and is in contact with the body of the patient. The wound-covering element 4 is provided at its periphery 8 with an adhesive surface 6 for gluing the device to the skin of the patient. The absorption body 2 consists of a layer 22 of a nonwoven-like textile material, which comprises cellulose fibers and is interspersed with super-absorbent particles (Super-Absorbing Polymers, SAP), in the present case with a copolymer of sodium acrylate and acrylic acid. Moreover, there is an accumulation of nanocrystalline, silver-containing substances, which have a microbiocidal effect. The cellulose fibers act as an interim storage system for the liquid quantities, which are acted upon spontaneously, and as a sort of transporting means, with which the wound secretions reach the super-absorber.

The layer 22 is surrounded by a liquid-permeable, also textile envelope 11, which has been closed by welding a peripheral seam 7 ultrasonically. As can be inferred particularly from FIG. 2, the envelope 11 has a peripheral overhang 50 of envelope material, which is located between the ultrasonic seam 7 and an outermost circumference 9 of the envelope 11. The overhang 30 is to prevent painful contact between the wound and the seam.

The film element 1, facing the wound, is made from a liquid-permeable, extremely thin, mucus membrane-compatible material. The film element 1 also contributes to protecting against contact with the ultrasonic seam 7.

Moreover, a connecting site 5.1 for evacuating gases and checking the vacuum is provided at the wound-covering element 4. According to FIGS. 1a to 1d and 2, the connecting site 5.1 is disposed approximately centrally. However, it may be located at any place on the wound-covering element, for example, in the vicinity of the periphery 8, as has been shown in FIG. 3.

Figure 7:
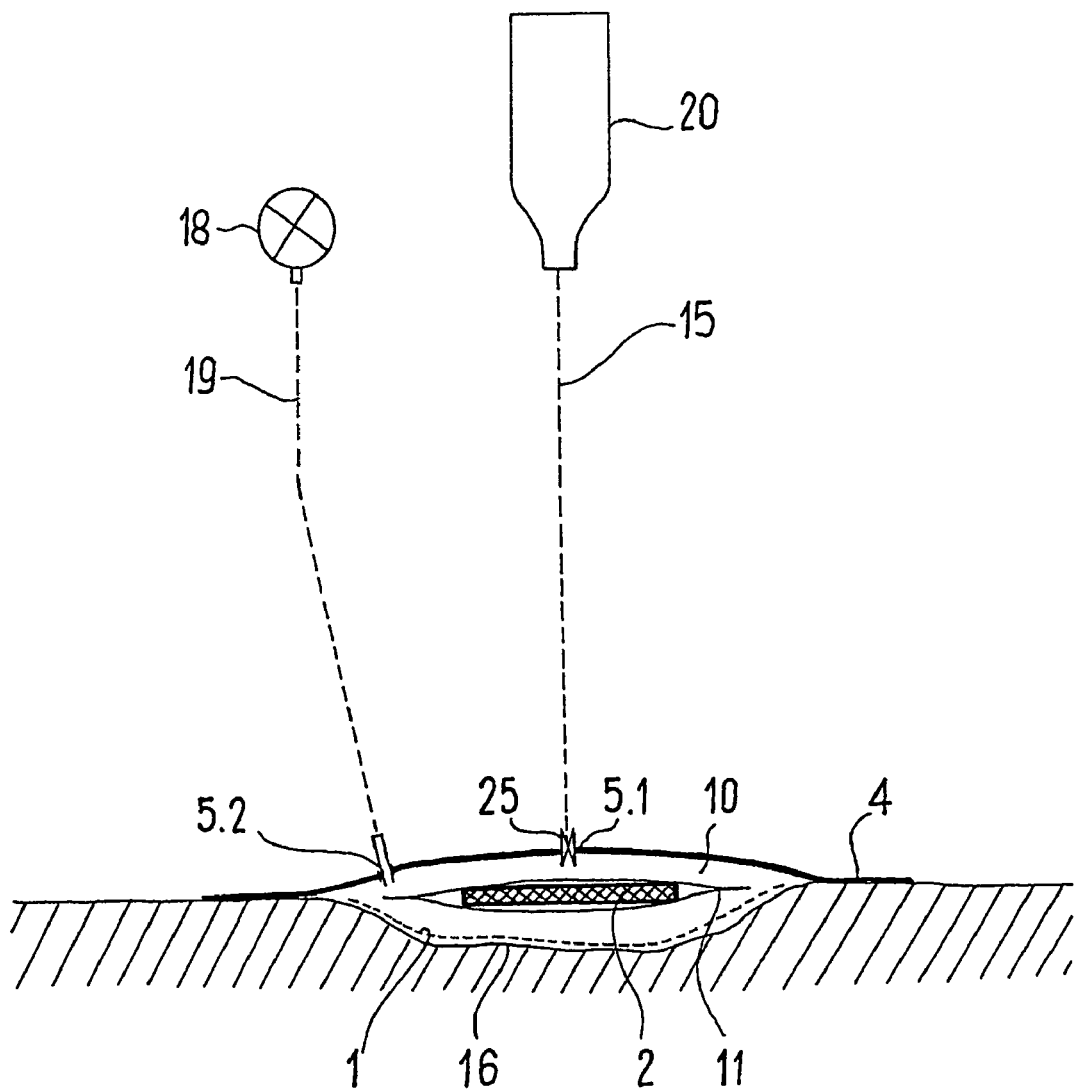
FIG. 7 shows the device of FIG. 1, however, with two connection sites, also in a diagrammatic section.

The device of FIG. 7 has two connecting sites 5.1, 5.2, of which the central one is for evacuating air and the second, lateral one for controlling the vacuum. A vacuum bottle 20 is connected over a hose line 15 to the central connecting site 5.1. On the other hand, a pressure manometer 18 is connected, also over a connecting hose 19, with the lateral connecting site 5.2. The description of FIG. 7 refers, of course to the device glued to the skin of the patient.

Figure 4:
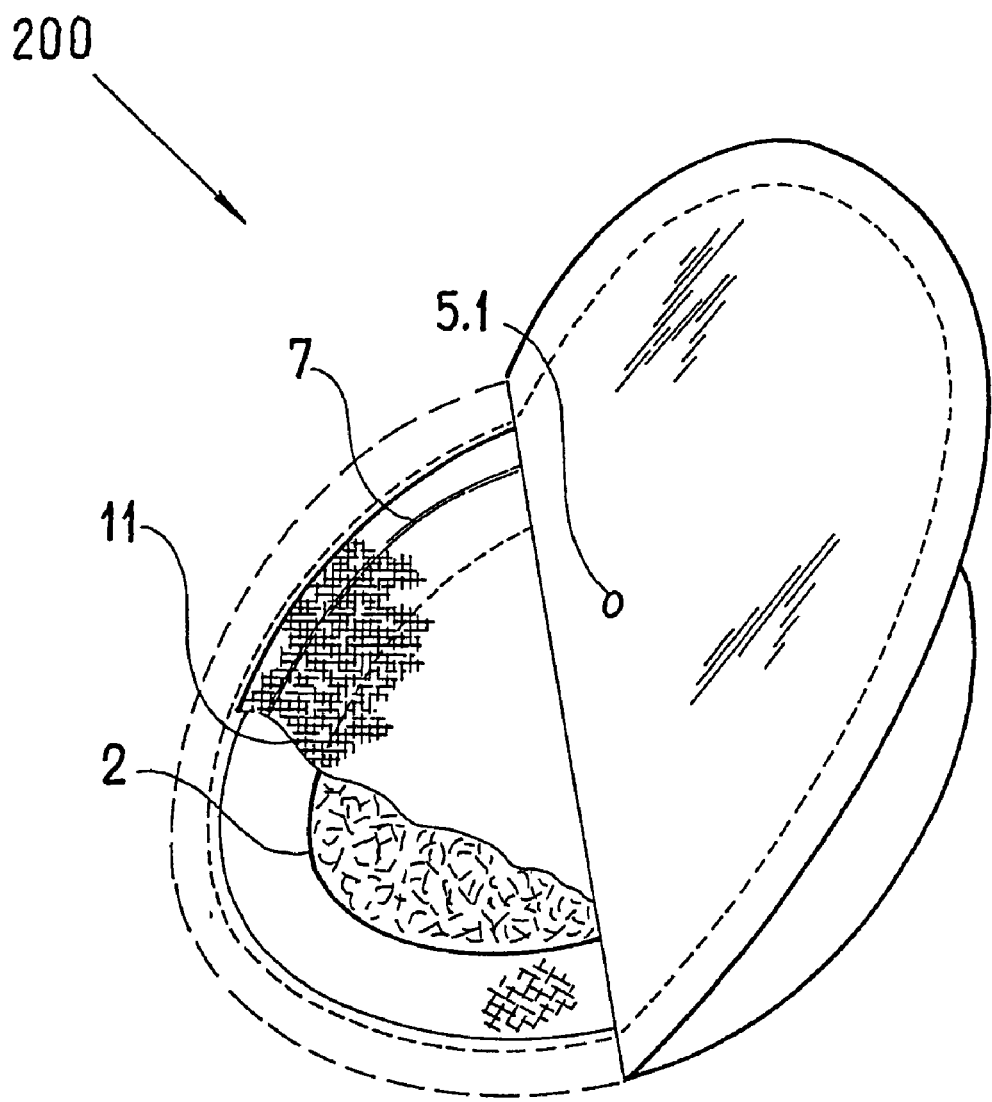
FIG. 4 shows a circular device for the treatment of wounds in plan view.
Figure 5:
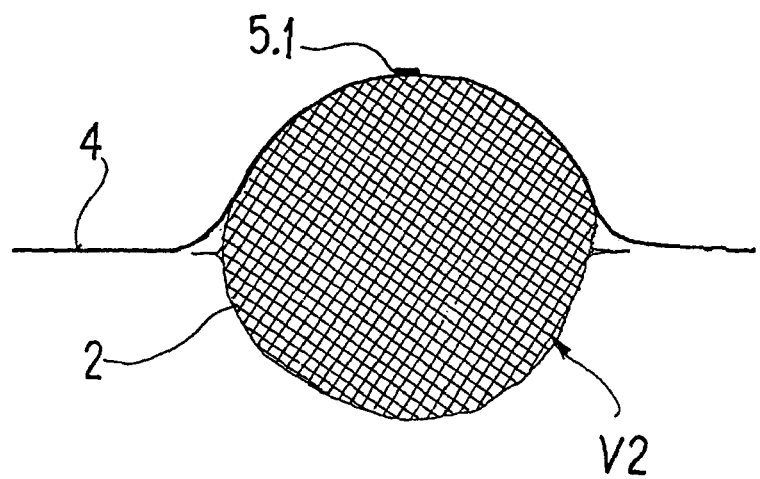
FIG. 5 shows a section A-A of FIG. 1d.

FIG. 4 shows a device 200, which differs from the device 100, shown in FIG. 1, only by its round or oval contour.

Figure 6:
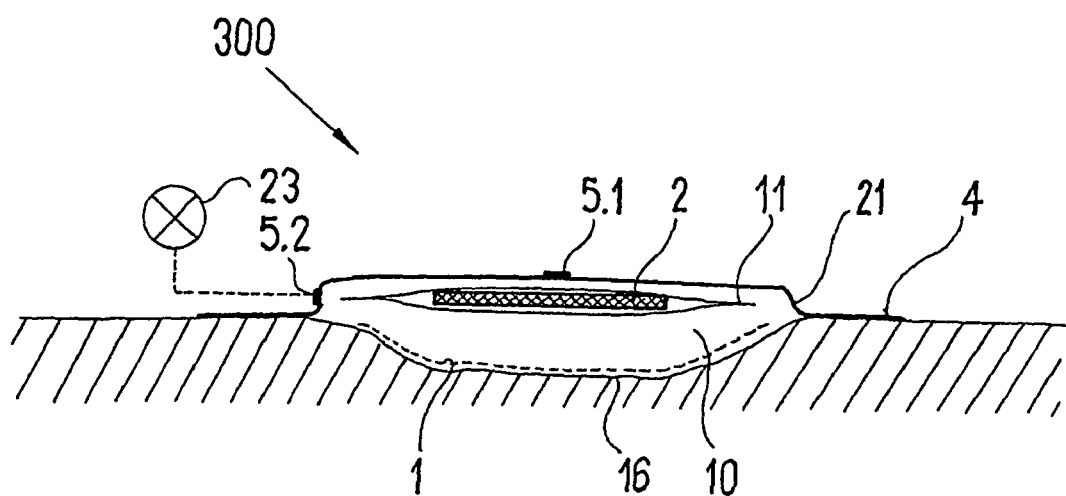
FIG. 6 shows a different embodiment of the device in a diagrammatic section.

A different embodiment (reference number 300) of the device is shown diagrammatically in FIG. 6. The device 300 has a shell-shaped wound-covering element 4, which makes it possible to introduce the connecting site 5.2 at its lateral casing 21. If necessary, a vacuum pump 23, optionally with a pressure regulator, maybe connected to the connecting site 5.2.

A silicone-coated pull-off film element 13 (compare FIG. 8) holds the parts of the device 100; 200 or 300 together and protects them against external effects. The area of the pull-off film element 13 is equal to that of the wound-covering element 4.

Figure 9:
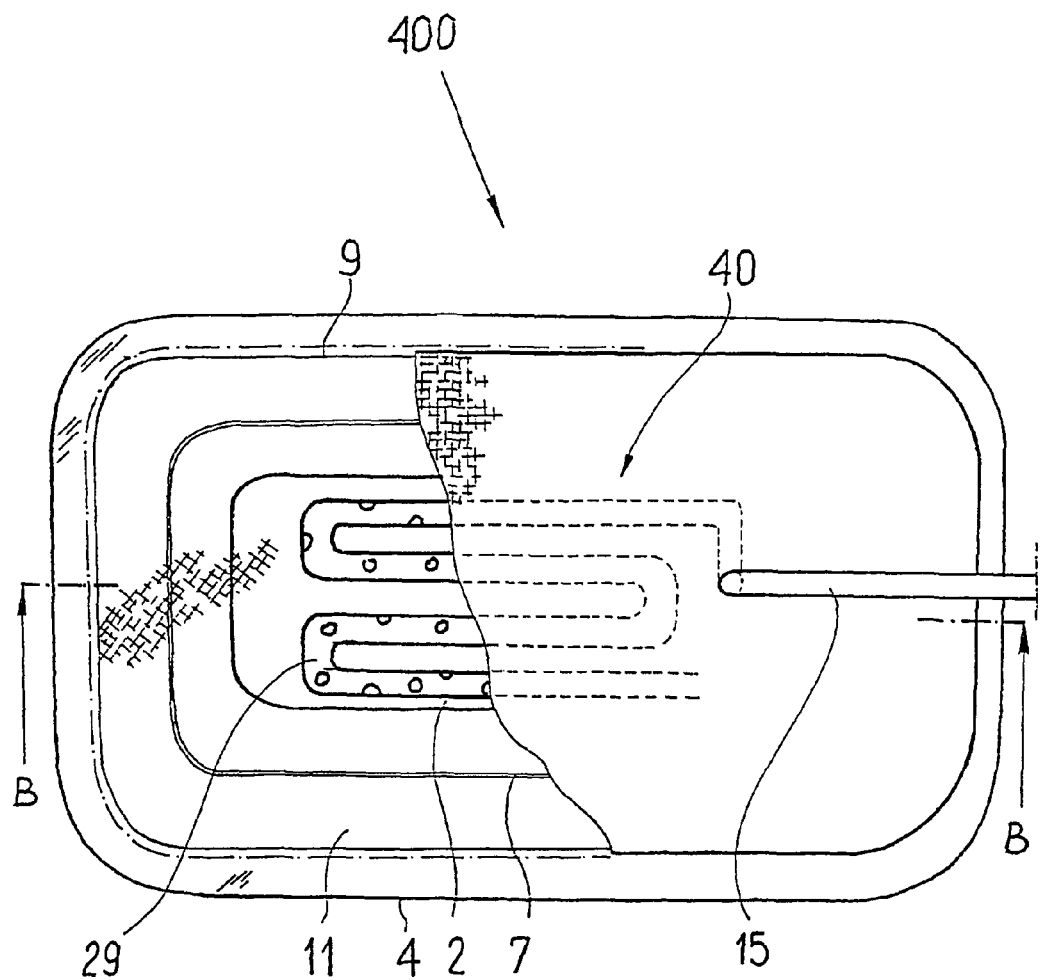
FIG. 9 shows a further embodiment of the device, with a pressure distributor, in a diagrammatic plan view of the flat side of the envelope.
Figure 10:
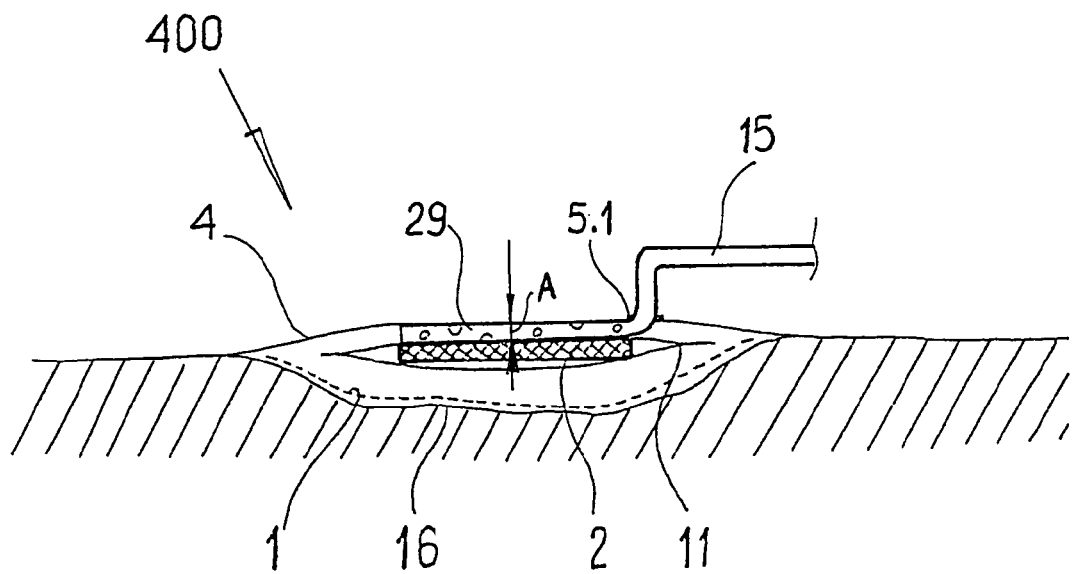
FIG. 10 shows a section B-B of FIG. 9.

As shown in FIGS. 9 and 10, the end piece 29 of the suction tube 15 is passed over the connecting site 5.1 and placed in meandering fashion between the film-like wound-covering element 4 and the envelope 11. The end piece 29 retains its given form and by being accommodated in an appropriately profiled template of an open cell foam, which is not shown. Accordingly, a configuration is created, for which the diameter of the end piece defines a required distance A between the wound-covering element 4 and the enveloped absorption body 2. The end piece 29 is provided in a manner, well-known, with several openings, which communicate with the pores of the template.

Figure 8:
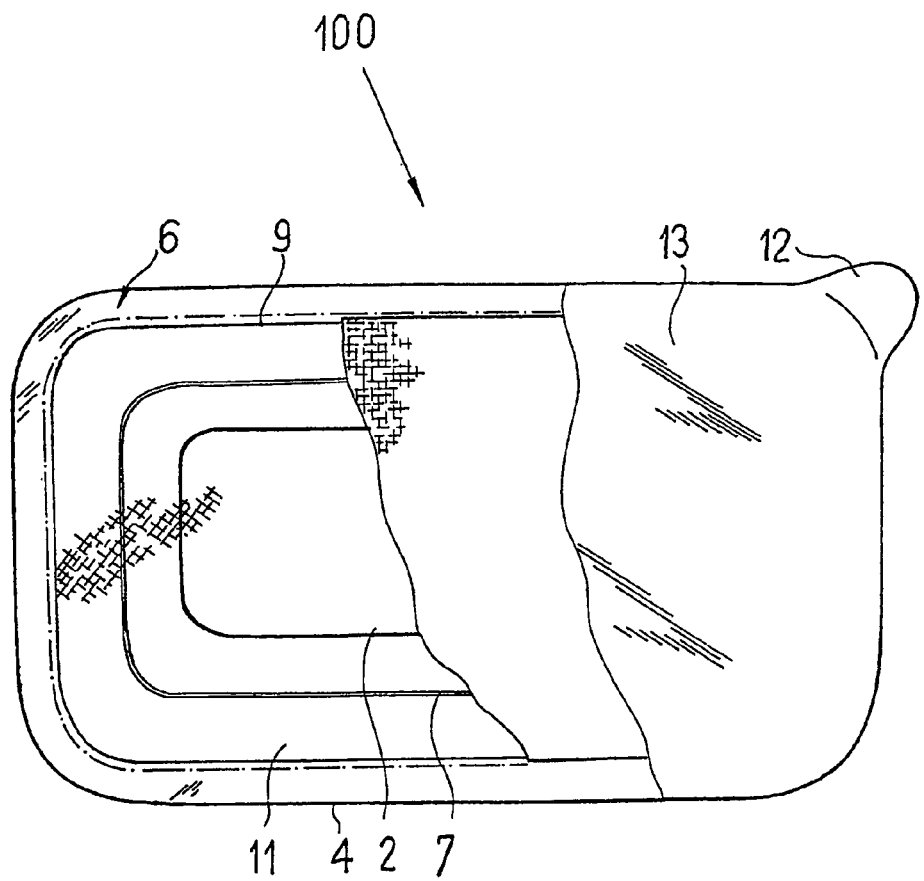
FIG. 8 shows the device of FIG. 1 in plan view of its back side.

Function:

A deep wound 16 is covered completely by gluing the device 100 (disposable device) of FIG. 1 to the skin of the patient. Previously, the pull-off film element 13, which is shown in FIG. 8 and exposes a peripheral adhesive surface 6 at the underside of the wound-covering element 4, was removed. To begin with, the mucous membrane-compatible film element 1 and then the flat absorption body 2 together with the envelope 11 were placed carefully on the wound surface with sterile forceps. Only then is the wound-covering element 4 glued around the wound. By gluing the device to the skin, a space 10 is formed between the wound-covering element 4 and the surface of the wound. A medical injections syringe 26 was connected over the aforementioned hose line 15 to the central connecting site 5.1, which is provided with a simple unidirectional check valve 25 (compare FIG. 1a) with a stopper. Since the space 10 is sealed, gases in it can be evacuated with the help of the injections syringe. This state is shown in FIG. 1b. The flat elements of the device rest on the wound surface. The vacuum, which has meanwhile been measured with the help of a vacuum indicator, which is not shown, was about 100 mm Hg. The cylindrical casing surface of the injection syringe may be provided with an appropriate, experimentally defined vacuum scale. The wound secretions, emerging from the wound, reached the absorption body 2 and bring about a compression beneath the wound covering element 4. After the aspiration of wound secretions, the volume of the absorption body 2 increases greatly (compare FIG. 1c). Since the area of the absorption body 2 is about 40% smaller than that of the envelope 11, it assumes a circular shape (compare FIG. 5).

By raising the pull-off tab 12 and with the help of the forceps, the consumed device 100 is now removed carefully from the region of the wound. If necessary, a new disposable device can be glued onto the wound with the help of forceps. The swelling process of the absorption body, used at the wound, has an advantageous effect on the healing process, since the absorption body, due to the increase in its weight, mechanically counteracts a hypergranulation of the wound tissue over the skin level in such a manner, in that a pressure situation, facing the center of the body of the patient, arises, which is added by the fixation under the aspirated outer film. In this way, the skin can be sutured more easily after the wound-healing process, since it does not protrude from the remaining skin level. This is also associated with certain cosmetic advantages.

There has thus been shown and described a novel device for the treatment of wounds using a vacuum which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. Device for treating wounds of a human or animal patient using a vacuum and comprising:

an air-tight wound-covering element, which, when placed in contact with the body of the patient, forms a wound space between the respective wound and the wound-covering element, at least one connecting site, which is in contact with the wound space and over which the air in the wound space can be evacuated, and at least one two-dimensional absorption body, which is to be disposed in the wound space underneath the wound covering element, the improvement wherein the absorption body is at least one layer of a textile section, which is enclosed in an envelope and interspersed with super-absorbing particles, the envelope being liquid permeable and having pores, the size of which essentially does not exceed that of the super-absorbing particles, the envelope comprising a peripheral overhang which extends along the entire periphery of the envelope, the absorption body, which is to be inserted in the wound space, has an initial volume (V1), which enlarges in the course of the absorption process and assumes a final volume (V2), such that, due to the size of the pores of the envelope, the absorbed wound secretions remain within the absorption body and, with that, below the wound covering element, until the absorption body is removed from the wound space, and in plan view, the layer has an area, which is 3% to 90% smaller than that of the envelope when placed flat.

2. The device of claim 1, wherein the absorption body is glued over its whole surface to the wound-covering element, a periphery at the wound-covering element being left free.

3. The device of claim 1, wherein the absorption body, when filled close to its capacity, approaches a circular shape in cross-section.

4. The device of claim 1, wherein the textile section of the absorption body consists of a nonwoven cellulose material.

5. The device of claim 1, wherein the wound-covering element is made of a material that does not shrink when in contact with the body of the patient.

6. The device of claim 1, wherein an external surface on the wound-covering element is capable of supporting an ink print.

7. The device of claim 1, wherein the connecting site has a valve.

8. The device of claim 1, wherein a pressure indicator is integrated in the device.

9. The device of claim 1, wherein the envelope of the absorption body is sewn on by ultrasonic seams.

10. The device of claim 1, wherein the absorption body, at its periphery, has an overhang of enveloping material.

11. The device of claim 1, wherein the absorption body, due to an increase in its weight, mechanically counteracts a hyper-granulation of wound tissue over a skin level of the patient and adds to a pressure caused by an aspiration wherein the pressure faces the center of the body of the patient.

12. The device of claim 1, wherein the peripheral overhang extends between a seam and an outermost circumference of the envelope.

13. The device of claim 1, further comprising a liquid-permeable, mucous membrane-compatible protective element, which, when placed in contact with the body of the patient, is disposed on a side of the absorption body opposite to the wound-covering element and, in plan view, is equal in area to the enveloped absorption body.

14. The device of claim 13, wherein at least one of the absorption body and the liquid-permeable protective element is exchanged when the device is in contact with the body of the patient.

15. The device of claim 13, wherein active substances, such as nanocrystalline silver particles, which affect the wound-healing process, are applied to at least one of the material of the absorption body and of the protective element.

16. The device of claim 13, wherein the protective element is film-like.

17. The device of claim 13, wherein the protective element is a section of textile material.

18. The device of claim 13, wherein the protective element comprises a foam material.

19. The device of claim 13, wherein the protective element comprises a loose bed of material pieces underneath the absorption body.

20. The device of claim 1, wherein the connecting site is connected to a hose line.

21. The device of claim 20, wherein a pressure manometer is connected directly to at least one of the connecting site and the hose line.

22. The device of claim 20, wherein at least one of a vacuum bottle and a vacuum pump is connected to the hose line.

23. The device of claim 20, wherein a piston and cylinder arrangement is connected to at least one of the connecting site and the hose line.

24. The device of claim 1, wherein a pressure distributor, contacting the envelope of the absorption body, is disposed below the wound covering element, yet above the enveloped absorption body.

25. The device of claim 24, wherein the pressure distributor is a template of a foam material, which is permeable to gases.

26. The device of claim 24, wherein the pressure distributor has a loop-like or meandering end piece of the suction tube passed through the connecting site, and wherein the end piece defines a distance (A) between the wound-covering element and the enveloped absorption body.

* * * * *